US008946409B2

(12) United States Patent
Becker et al.

(10) Patent No.: US 8,946,409 B2
(45) Date of Patent: Feb. 3, 2015

(54) POLYCYCLIC β LACTAM DERIVATIVES FOR THE TREATMENT OF CANCER

(75) Inventors: Frederick F. Becker, Houston, TX (US); Bimal K. Banik, Edinburg, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/982,101

(22) PCT Filed: Jan. 27, 2012

(86) PCT No.: PCT/US2012/022935
§ 371 (c)(1),
(2), (4) Date: Nov. 6, 2013

(87) PCT Pub. No.: WO2012/103456
PCT Pub. Date: Aug. 2, 2012

(65) Prior Publication Data
US 2014/0066423 A1    Mar. 6, 2014

Related U.S. Application Data

(60) Provisional application No. 61/436,934, filed on Jan. 27, 2011.

(51) Int. Cl.
*C07D 205/08* (2006.01)
*C07D 401/04* (2006.01)

(52) U.S. Cl.
CPC ................................. *C07D 401/04* (2013.01)
USPC ........................................................ 540/354

(58) Field of Classification Search
USPC ........................................................ 540/354
See application file for complete search history.

(56) References Cited

U.S. PATENT DOCUMENTS

| | | | |
|---|---|---|---|
| 6,225,463 | B1 | 5/2001 | De Vos et al. |
| 7,635,693 | B2 | 12/2009 | Dou et al. |
| 2005/0107430 | A1 | 5/2005 | Banik et al. |

OTHER PUBLICATIONS

Banik et al. Journal of Medicinal Chemistry (2003), 46(1), 12-15.*
Banik, et al., "Asymmetric synthesis of anticancer β-lactams via Staudinger reaction: Utilization of chiral ketene from carbohydrate," *European Journal of Medicinal Chemistry*, 45:846-848, 2010.
Banik, et al., "Novel Anticancer β-Lactams," in Topics in Heterocyclic Chemistry: Heterocyclic Scaffolds I, Bimal K. Banik, Ed., 22:349-373, 2010.
Banik, et al., "Stereocontrolled synthesis of anticancer β-lactams via the Staudinger reaction," *Bioorganic & Medicinal Chemistry*, 13:3611-3622, 2005.
Banik, et al., "Stereoselective synthesis of β-lactams with polyaromatic imines: Entry into new and novel anticancer agents," *J. Med. Chem.*, 46:12-15, 2003.
Banik, et al., "Stereospecific glycosylation via Ferrier Rearrangement for optical resolution," *J. Org. Chem.*, 59(17):4714-4716, 1994.
Banik, et al., "Synthesis of anticancer β-lactams: mechanism of action," *Bioorganic & Medicinal Chemistry*, 12:2523-2528, 2004.
Banik, et al., "Unprecedented stereoselectivity in the Staudinger reaction with polycyclic aromatic imines," *Tetrahedron Letters*, 41:6551-6554, 2000.
Banik, et al., "Versatile β-lactam synthons: enantiospecifc synthesis of (−)-polyoxamic acid," *J. Org. Chem.*, 58(2):307-309, 1993.
Banik, In: *β-Lactams: Synthesis, Stereochemistry, Synthon, and Biological Evaluation*, Bentham Sci. Publ. Ltd., vol. 11, 2004.
Bose, et al., "Polyhydroxy Amino Acid Derivatives via β-Lactams Using Enantiospecific Approaches and Microwave Techniques," *Tetrahedron Symposium*, 56:5603-5619, 2000.
Bose, et al., In: *The Amide Linkage: Selected Structural Aspects in Chemistry, Biochemistry, and Material Science*, Greenberg, et al., (Eds.), Wiley-Interscience, NY, 7:157-214, 2000.
Burnett, "β-Lactam Cholesterol Absorption Inhibitors," *Curr. Med. Chem.* 11:1873-1887, 2004.
Burnett, et al., "2-Azetidinones as Inhibitors of Cholesterol Absorption," *J. Med. Chem.*, 37(12):1733-1736, 1994.
Buynak, "The Discovery and Development of Modified Penicillin- and Cephalosporin-Derived β-Lactamase Inhibitors," *Curr. Med. Chem.*, 11:1951-1964, 2004.
Clader, "The Discovery of Ezetimib: A View from Outside the Receptor," *J. Med. Chem.*, 47(1):1-9, 2004.
Clader, et al., "2-Azetidinone Cholesterol Absorption Inhibitors: Structure-Activity Relationships on the Heterocyclic Nucleus," *J. Med. Chem.*, 39:3684-3693, 1996.
Finke et al., "Orally Active β-Lactam Inhibitors of Human Leukocyte Elastase. 3. Stereospecific Synthesis and Structure-Activity Relationships for 3,3-Dialkylazetidin-2-ones," *J. Med. Chem.*, 38:2449-2462, 1995.
Georg and Ravikumar, In: *The Organic Chemistry of β-Lactams*, VCH publishers, NY, 1992.
Glazer et al., "Noninvasive Radiofrequency Field Destruction of Pancreatic Adenocarcinoma Xenografts Treated with Targeted Gold Nanoparticles," *Clin Cancer Res.*, 16(23):5712-5721, 2010.
Kidwai et al., "Synthetic Strategies and Medicinal Properties of β-Lactams," *Curr. Med. Chem.*, 6:195-215, 1999.
Manhas et al., "Vinyl-β-lactams as Efficient Synthons. Eco-friendly Approaches via Microwave Assisted Reactions," *Tetrahedron, Symposium*, 56:5587-5601, 2000.
Ojima, "Recent Advances in the β-Lactam Synthon Method," *Acc. Chem. Res.*, 28(9):383-389, 1995.
PCT International Search Report and Written Opinion issued in International Application No. PCT/US2012/022935, dated Aug. 24, 2012.
Southgate et al., In: *Recent Progress in the Chemical Synthesis of Antibiotics and Related Microbial Products*, Lukacs (Ed.), Springer-Verlag, Berlin, 621(2), 1993.

(Continued)

*Primary Examiner* — Nizal Chandrakumar
(74) *Attorney, Agent, or Firm* — Parker Highlander PLLC

(57) ABSTRACT

Provided herein are polycyclic β-lactam compounds, compositions thereof and methods for the treatment and prevention of diseases such as cancer, including pancreatic cancer and pancreatic cancers resistant to mainline chemotherapeutic agents.

6 Claims, 9 Drawing Sheets

(56) References Cited

OTHER PUBLICATIONS

Stadel et al., "TRAIL-Induced Apoptosis is Preferentially Mediated via TRAIL Receptor 1 in Pancreatic Carcinoma Cells and Profoundly Enhanced by XIAP Inhibitors," *Clin Cancer Res.*, 16(23):5734-5749, 2010.

STN Database entry for CAS Registry No. 1135236-18-8, dated Apr. 16, 2009.

Suffness, In: *Taxol Science and Applications*, CRC Press, Boca Raton, FL, 1995.

Wan et al., "Surface-Immobilized Aptamers for Cancer Cell Isolation and Microscopic Cytology," *Cancer Res.*, 70(22):9371-9380, 2010.

* cited by examiner

POLYCYCLIC β LACTAM DERIVATIVES FOR THE TREATMENT OF CANCER

This application is a national phase application under 35 U.S.C. §371 of International Application No. PCT/US2012/022935, filed Jan. 27, 2012, which claims priority to U.S. Provisional Application No. 61/436,934, filed Jan. 27, 2011. The entire text of each of the above referenced disclosures is specifically incorporated herein by reference.

This invention was made with government support under grant numbers NIH/NCI P20CA138022 and NIH-SCORE 2S06M008038-37, awarded by the National Institute of Health. The government has certain rights in the invention.

BACKGROUND OF THE INVENTION

I. Field of the Invention

The present disclosure relates generally to the fields of chemistry, biology and medicine. More particularly, it concerns β-lactam compounds, compositions and methods for the treatment and prevention of diseases such as cancer, including pancreatic cancer and gemcitabine-resistant pancreatic cancer.

II. Description of Related Art

Pancreatic cancer is a malignant neoplasm of the pancreas. The prognosis is poor. Save in the lesser instance of success when these tumors are diagnosed early and in highly localized presentation the vast majority of patients die in a relatively short time. In part this is because the cancer usually causes no symptoms early on, leading to locally advanced or metastatic disease at time of diagnosis. Complete remission is still rare. Several human pancreatic cancer lines are highly resistant to gemcitabine (GEM). Accordingly, identifying and developing therapies that may be used to treat this disease would be highly desirable.

In general, β-lactams have many medicinal applications (Southgate et al., 1993; Kidwai et al., 1999; Bose et al., 2000; Banik, 2004). The need for potent β-lactam antibiotics and effective β-lactamase inhibitors has challenged chemists to design novel β-lactams (Buynak, 2004). These compounds have served as useful in the preparation of many heterocyclics of medicinal significance (Manhas et al., 2000; Bose et al., 2000; Ojima, 1995; Banik et al., 1994; Banik et al., 1993). Hydroxy β-lactam derivatives have been used as the starting materials in the semi synthesis of paclitaxel (Taxol) and docetaxel (Taxotere) (Suffness, 1995). The clinical use of β-lactams as therapeutic agents for lowering plasma cholesterol levels has been published (Clader et al., 1996; Burnett et al., 1994; Burnett, 2004; Clader, 2004). The biological activities of β-lactams against human leukocyte elastase have also been reported (Finke et al., 1995). Developing new β-lactams analogs, especially ones with potent anti-cancer properties, would be highly desirable.

Despite decades of the most intensive research and clinical efforts, our increasing ability to identify molecular targets putatively associated with key pathways in the development and lethal spread of cancer, and a myriad of claims of success, our struggle to contain, reverse or as in our most extreme expectations cure cancer have proven to be minimally successful. In the majority of human tumors derived from origins in various organs we have been able to slow recurrence, alleviate symptoms to a minor degree and delay death. On top of this dismaying picture, drugs that appeared to have a logical mode of action and initially promising results often prove to be of minimal efficacy and are removed from availability. The anti-angiogenic drug Avastin has been removed from use against breast cancer within the month (December 2010).

To further intensify this dilemma there are human cancers such as those arising in the pancreas and glioblastoma of the brain for which no available therapy is currently available. The National Cancer Institute has published estimates that 18,770 men and 18,030 women in the United States would die of pancreatic cancer annually. When compared with a detection rate of approximately 45,000 cases per year this demonstrates the devastating effect of this tumor. It represents the fourth leading cause of deaths worldwide. The median survival duration from diagnosis to death is approximately 6 months and the overall five-years survival is less than 5% (Jia et al., 2010; Li and Abbruzzese, 2010; Tran et al., 2010).

In addition to its early silent growth, treatment is complicated by its initial resistance to almost all available drugs and it remarkable ability to develop resistance to available mainline therapies within months of the onset of treatment (Tran et al., 2010; Kunnumakkara et al., 2010). Despite the most intensive investigation using all target pathways (Wan et al., 2010; Glazer et al., 2010 and Stadel et al., 2010) there is not a single agent available that has any significant effect on growing pancreatic cancer cells in animals or humans.

SUMMARY OF THE INVENTION

The present disclosure provides novel compounds β-lactam derivatives with potent anti-cancer properties. Methods for their use for the treatment of disease, including pancreatic cancer, and methods of their manufacture are also disclosed herein.

In one aspect, the present disclosure provides compounds of the formula:

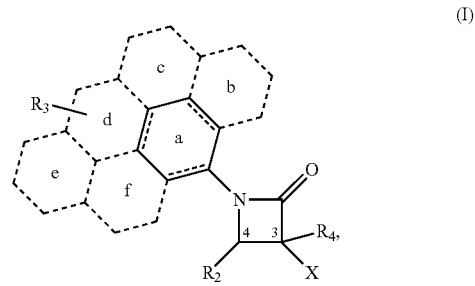

(I)

wherein:
X is —OS(O)$_2$R$_1$, —S(O)$_2$NH$_2$, —C(O)NH$_2$ or guanidinyl,
  wherein:
    R$_1$ is alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq8)}$, heteroaralkyl$_{(C\leq8)}$, or a substituted version of any of these groups;
R$_2$ is alkyl$_{(C\leq12)}$, aralkyl$_{(C\leq12)}$, heteroaryl$_{(C\leq12)}$, heteroaralkyl$_{(C\leq12)}$, or a substituted version of any of these groups;
R$_3$ and R$_4$ are each independently:
  amino, azido, cyano, halo, hydrogen, or hydroxy; or
  alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, aryloxy$_{(C\leq12)}$, aralkoxy$_{(C\leq12)}$, acyloxy$_{(C\leq12)}$, alkylamino$_{(C\leq12)}$, dialkylamino$_{(C\leq12)}$, amido$_{(C\leq12)}$, or a substituted version of any of these groups; and
rings b, c, d, e and f, if present, are aromatic;
or a pharmaceutically acceptable salt or tautomer thereof.

In some embodiments, X is —OS(O)$_2$R$_1$. In some embodiments, R$_1$ is methyl. In some embodiments, R$_2$ is heteroaryl$_{(C\leq12)}$. In some embodiments, R$_2$ is pyridyl. In some embodiments, $R_3$ is hydrogen. In some embodiments, $R_4$ is hydrogen. Further embodiments of compounds provided by this invention are provided in the section entitled "Description of Illustrative Embodiments" below. For example, in some embodiments, the compound is further defined as:

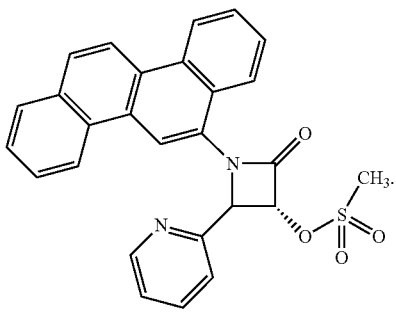 [SMILES: CS(=O)(=O)O[C@H]1C(=O)N(c2cc3c4ccccc4ccc3c3ccccc23)C1c1ccccn1]

In another aspect, the present disclosure provides pharmaceutical compositions comprising an excipient and one of a compound from those described above or discussed in the section entitled "Description of Illustrative Embodiments" below. In some embodiments, the compound is present in at least 85% enantiomeric excess. In some embodiments, the compound is present in at least 90% enantiomeric excess. In some embodiments, the compound is present in at least 95% enantiomeric excess.

In another aspect, the present disclosure provides methods for inducing apoptosis of hyperproliferative cells comprising administering to the cells an effective amount of a compound selected from those described above or discussed in the section entitled "Description of Illustrative Embodiments" below. In some embodiments, the cells were identified as hyperproliferative based on an evaluation of the physical, chemical or biological properties of the cells. In some embodiments, the cells were obtained from a tissue biopsy from a patient suspected of having a hyperproliferative disease. In some embodiments, the hyperproliferative cells are cancer cells, for example, wherein the cancer is colorectal, breast, pancreatic, brain, lung, stomach, a blood, skin, testicular, prostate, ovarian, liver, esophageal, cervical, head, neck, non-melanoma skin, neuroblastoma or glioblastoma. In some embodiments, the cells are pancreatic cancer cells. In some of these embodiments, the pancreatic cancer is resistant to gemcitabine. In some embodiments, the cells are in a patient.

In another aspect, the present disclosure provides methods for treating a hyperproliferative disease in a patient in need thereof comprising administering to the patient an effective amount of a compound selected from those described above or discussed in the section entitled "Description of Illustrative Embodiments" below. In some embodiments, the patient was identified as having a hyperproliferative disease based on evaluation of a biological sample from the patient. In some embodiments, the test comprises evaluating a physical, chemical or biological property of the biological sample from the patient. In some embodiments, the biological sample is obtained from a tissue biopsy. In some embodiments, the hyperproliferative disease is cancer. In some embodiments, the cancer is colorectal cancer, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, neuroblastoma and glioblastoma. In some embodiments, the cancer is pancreatic cancer. In some embodiments, the pancreatic cancer is resistant to gemcitabine. In some embodiments, the pancreatic cancer is resistant to gemcitabine and a number of other mainline chemotherapeutic agents. In some embodiments, the compound is administered orally. In some embodiments, the effective amount of compound is 500 mg/day. In some embodiments, the compound is administered intravenously or intratumorally. In some embodiments, the effective amount of compound is from about 0.05 to about 5.0 g/m²/day. In some embodiments, the compound is administered orally. In some embodiments, the compound is formulated as a hard or soft capsule or as a tablet. In some embodiments, the compound is administered at least once a day. In some embodiments, the compound is administered up to six times a day. In some embodiments, the effective amount of the compound is from about 10 to about 1500 mg/day. In some embodiments, the effective amount of the compound is from about 25 to about 400 mg/day.

In another aspect, the present invention provides methods for the preparation of a compound of formula I comprising:
(i) reacting a starting material of the formula:

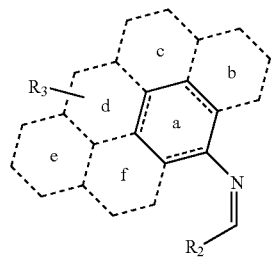

with acetoxyacetyl chloride and a first organic base to form a trans-lactam intermediate;
(ii) hydrolyzing the trans-lactam intermediate in aqueous base to form a hydroxy intermediate; and
(iii) reacting the hydroxy intermediate with a reagent selected from the group consisting of $R_1SO_2Cl$, $Cl—S(O)_2NH_2$, $Cl—C(O)NH_2$ and Cl-guanidinyl, and a second organic base to form a compound selected from those described above or discussed in the section entitled "Description of Illustrative Embodiments" below.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

Figure 1:
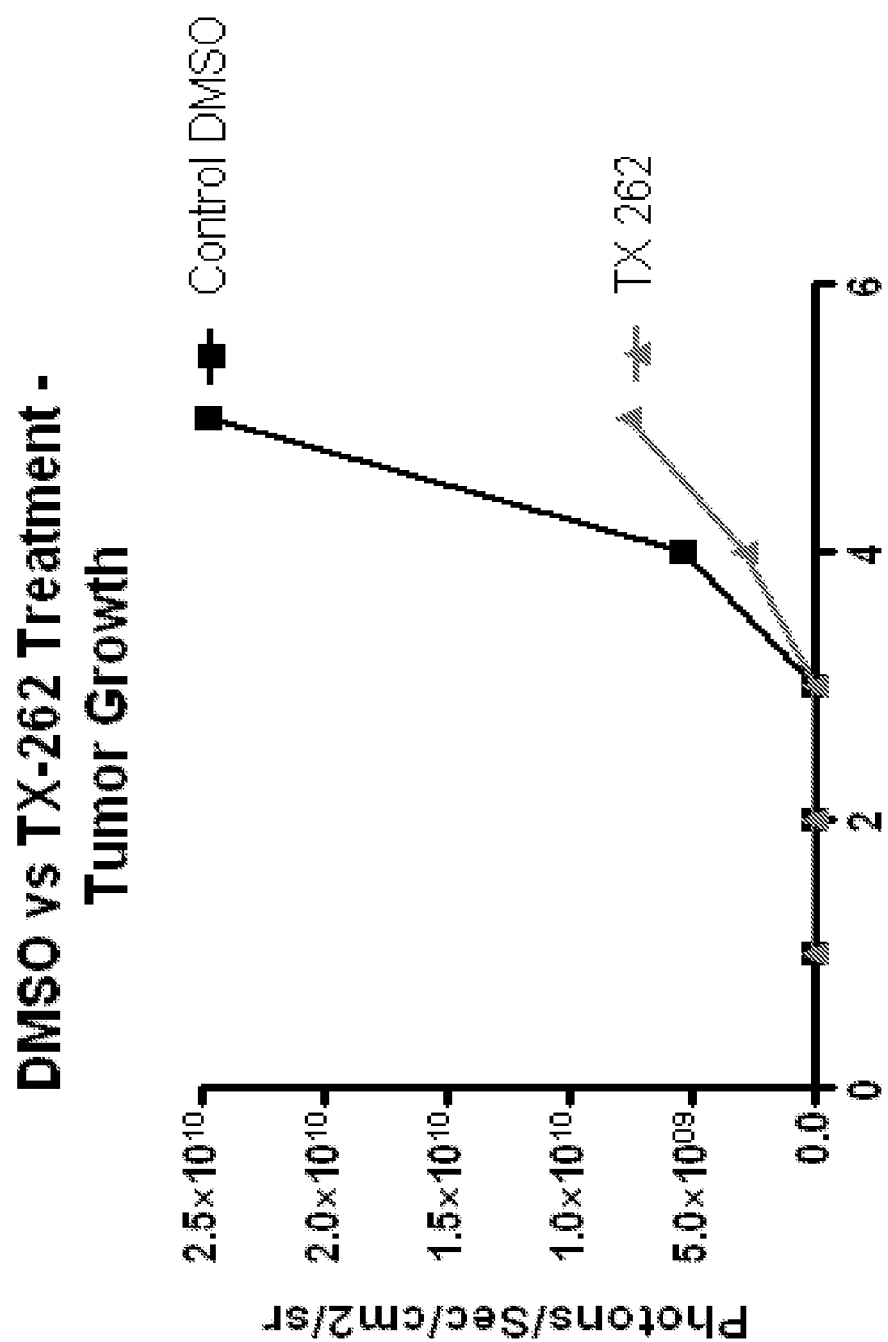
FIG. 1: The measurement of the average tumor mass from TX-262 treated and control mice at 4 and 5 weeks. Viable tumor mass in TX-262 treated mice was approximately 33% of that in control mice at 5 weeks.
Figure 2:
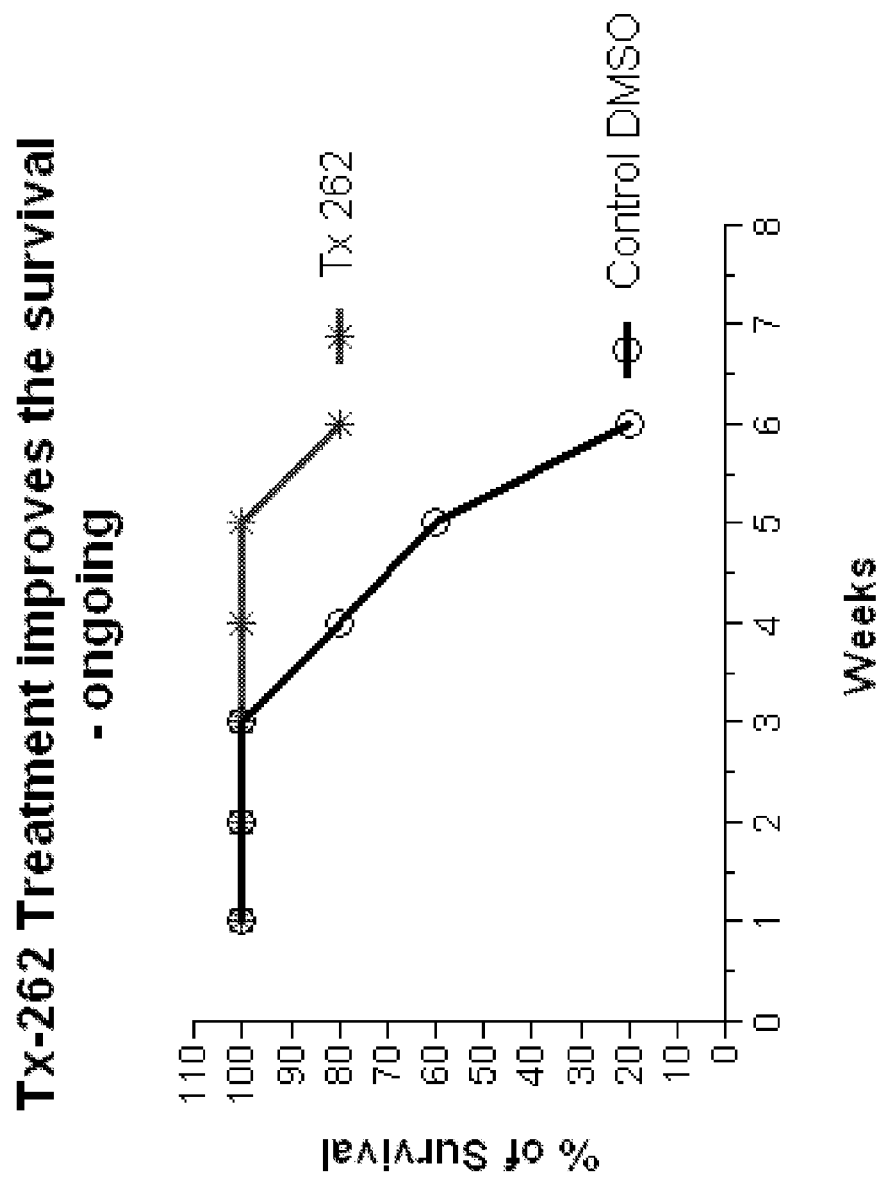
FIG. 2: At 6 weeks only 20% of control mice survived while 80% of TX-262 treated mice were still viable.
Figure 3:
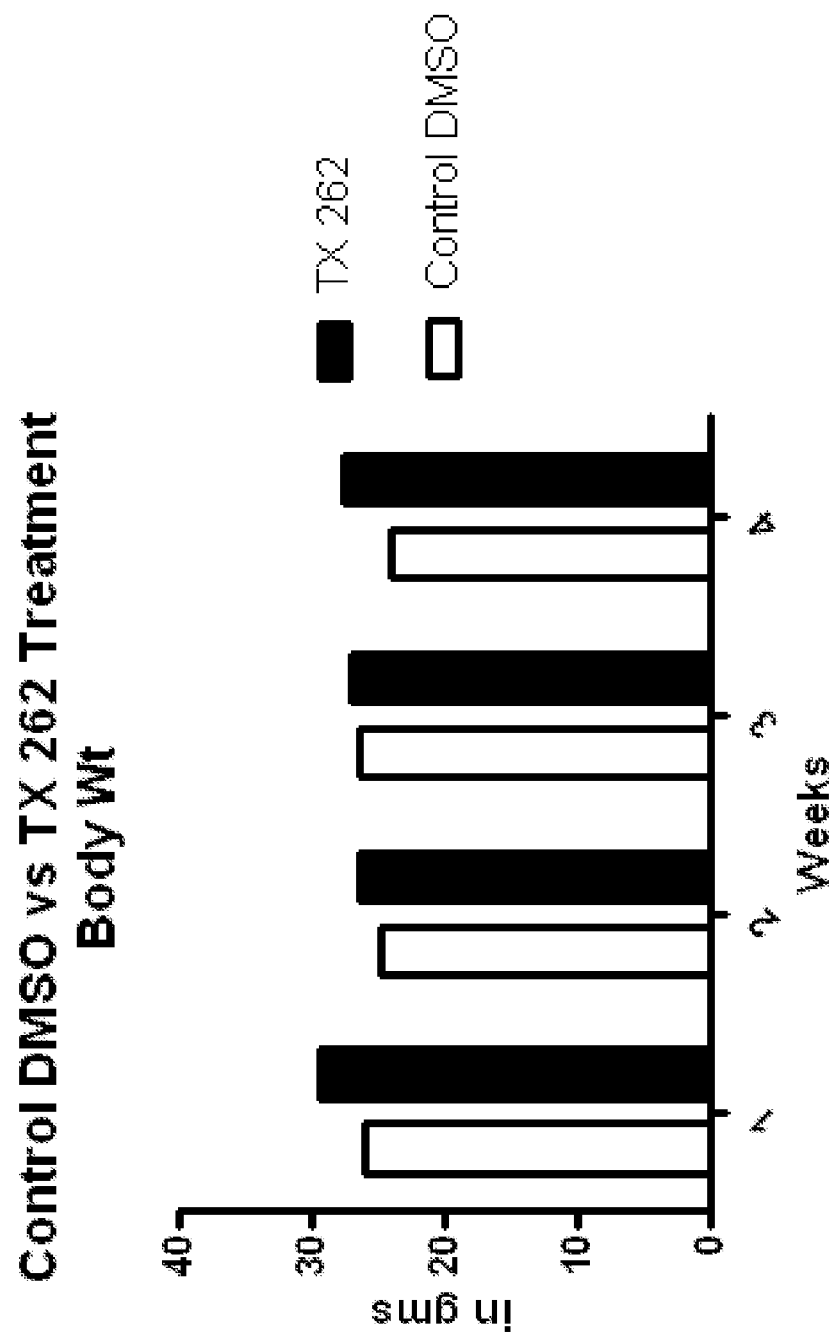
FIG. 3: Weights of mice were determined weekly through the treatment regimen. No significant differences between control and treated mice were seen. This suggested that TX-262 did not induce any significant toxicity throughout treatment.
Figure 4:
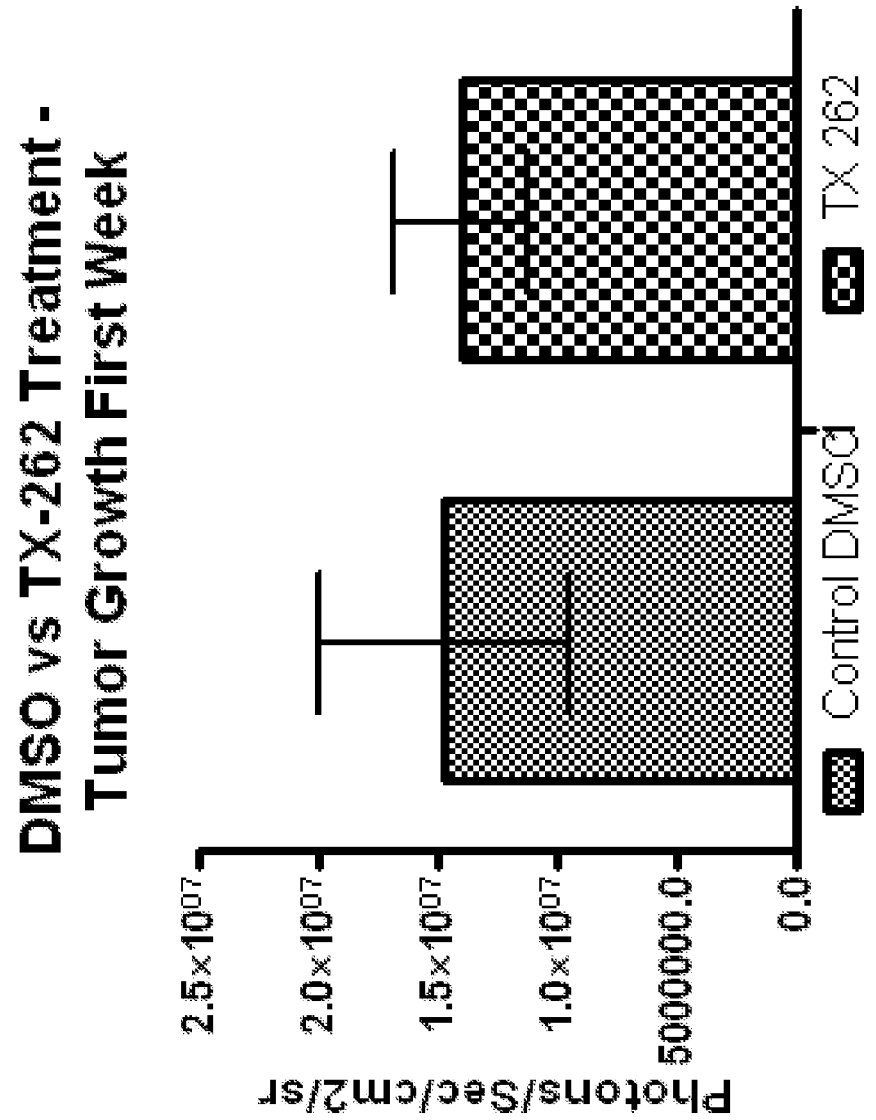
FIGS. 4-8: These figures demonstrate the detailed determinations on the tumor mass in the control and TX-262 treated mice from the first through the fifth weeks.
Figure 5:
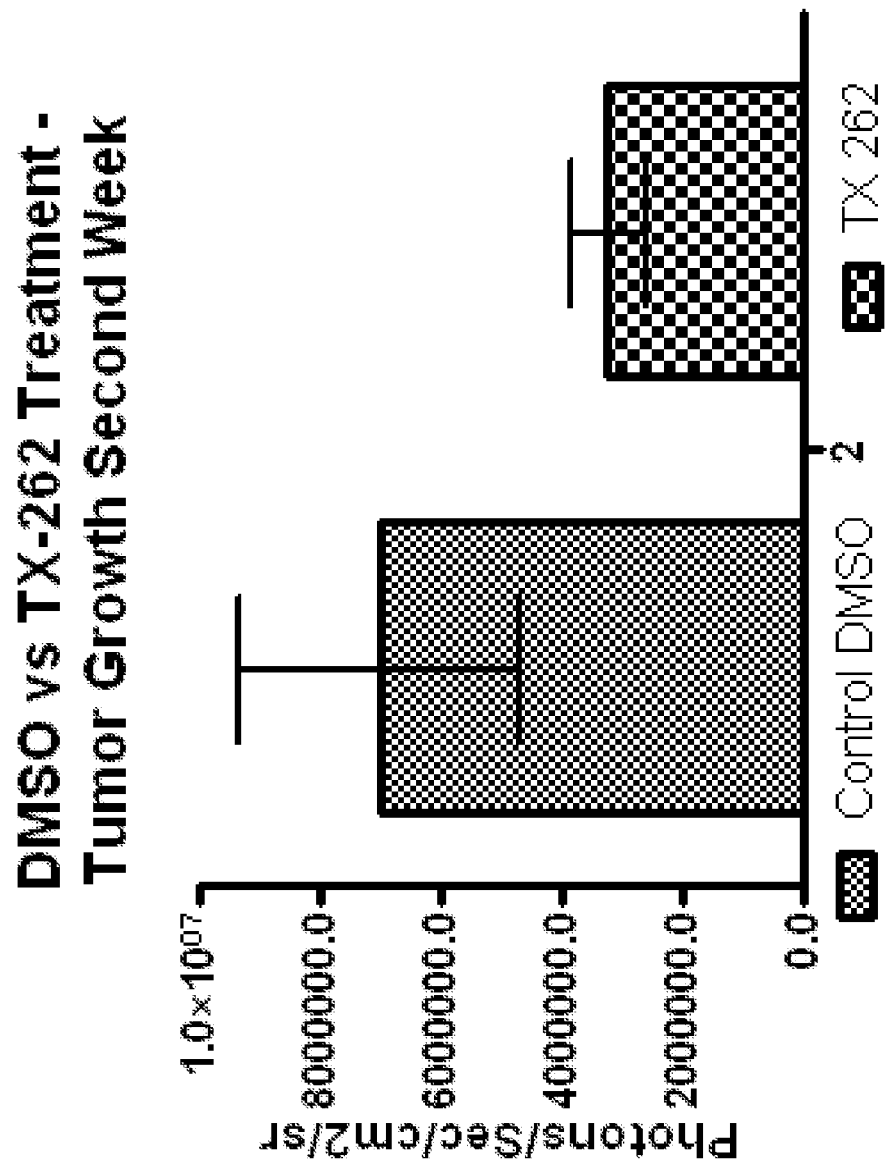
Figure 6:
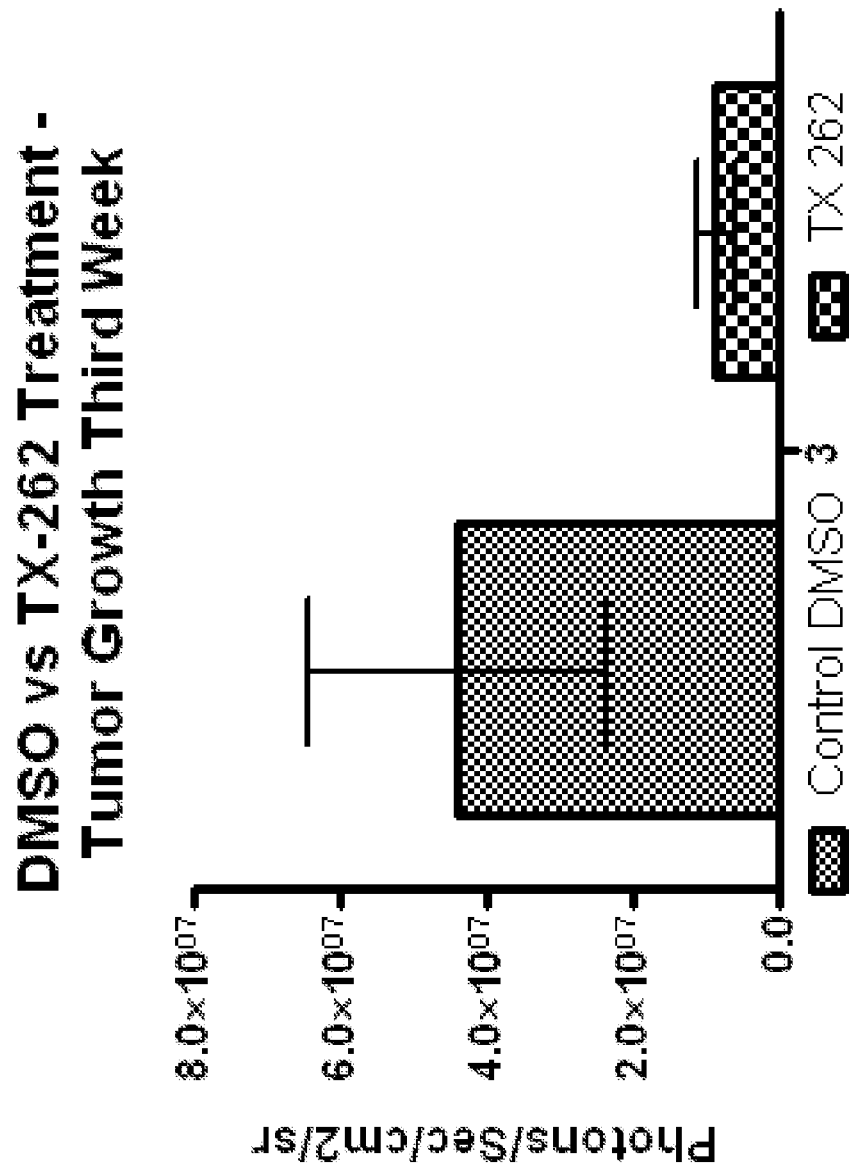
Figure 7:
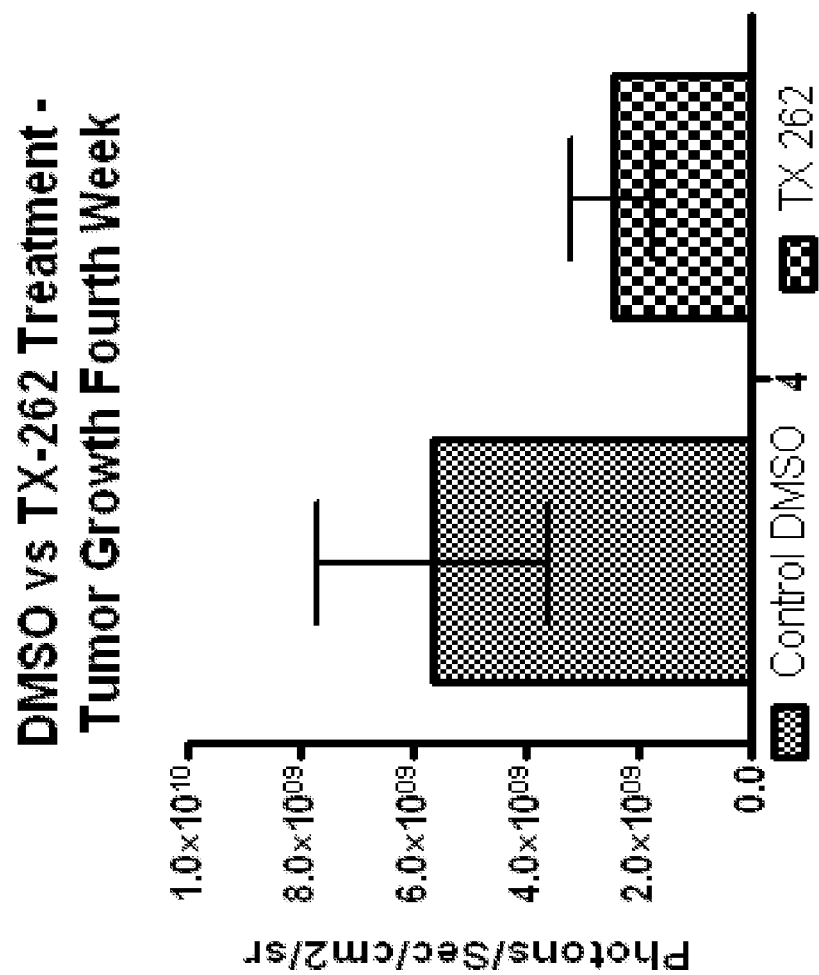
Figure 8:
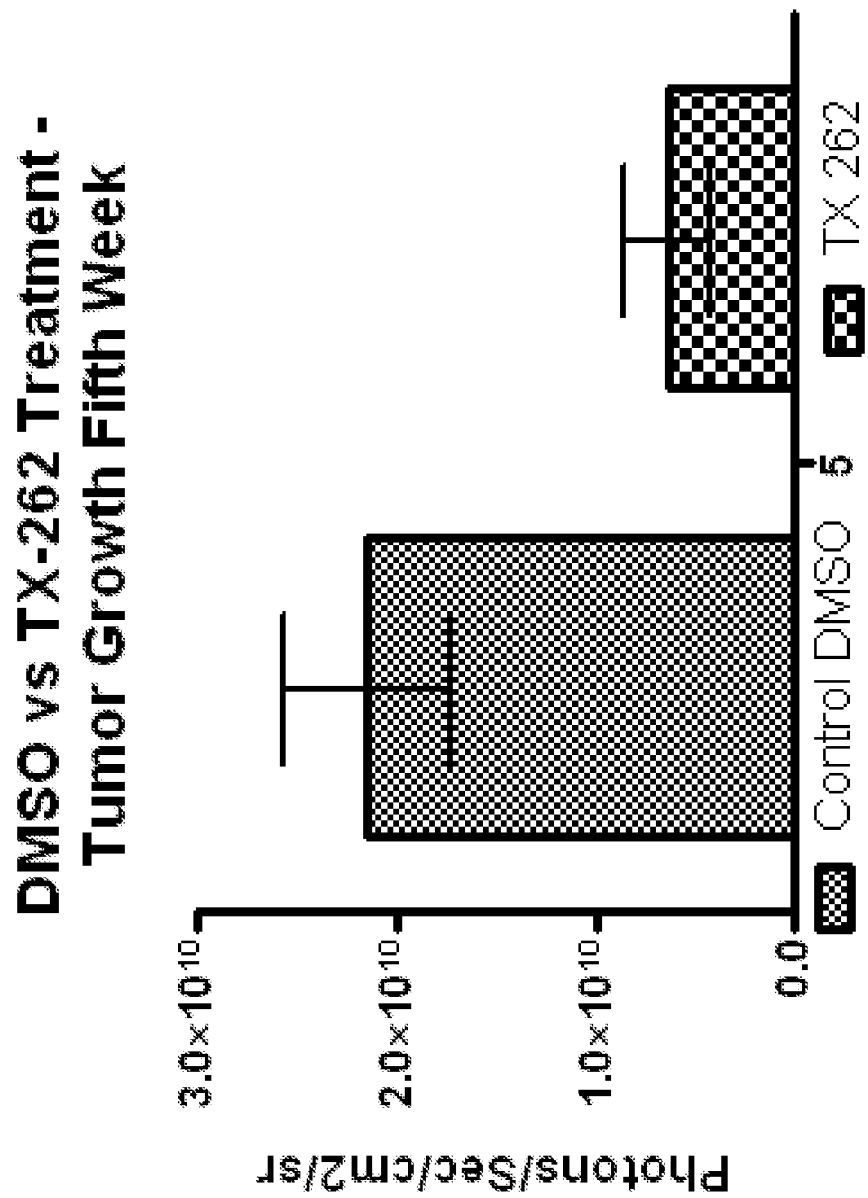

The present disclosure provides novel β-lactam compounds with potent anti-cancer properties. Methods for their use for the treatment of disease, including pancreatic cancer and gemcitabine-resistant pancreatic cancer are also provided. Methods for the manufacture of these compounds are also disclosed herein.

I. DEFINITIONS

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —SiH$_3$ (see below for definitions of group(s) containing the term silyl, e.g., alkylsilyl).

The symbol "—" means a single bond, "=" means a double bond, and "≡" means triple bond. The symbol "----" represents an optional bond, which if present is either single or double. The symbol "====" represents a single bond or a double bond. The symbol "⁓", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂▬" means a single bond where the group attached to the thick end of the wedge is "out of the page." The symbol "⫾⫾⫾⫾" means a single bond where the group attached to the thick end of the wedge is "into the page". The symbol "⁓" means a single bond where the conformation is unknown (e.g., either R or S), the geometry is unknown (e.g., either E or Z) or the compound is present as mixture of conformation or geometries (e.g., a 50%/50% mixture).

When a group "R" is depicted as a "floating group" on a ring system, for example, in the formula:

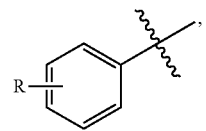

then R may replace any hydrogen atom attached to any of the ring atoms, including a depicted, implied, or expressly defined hydrogen, so long as a stable structure is formed.

When a group "R" is depicted as a "floating group" on a fused ring system, as for example in the formula:

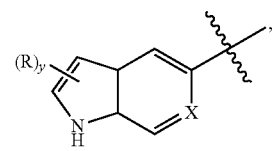

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

When y is 2 and "(R)$_y$" is depicted as a floating group on a ring system having one or more ring atoms having two replaceable hydrogens, e.g., a saturated ring carbon, as for example in the formula:

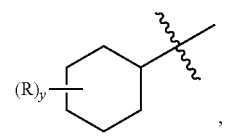

then each of the two R groups can reside on the same or a different ring atom. For example, when R is methyl and both R groups are attached to the same ring atom, a geminal dimethyl group results. Where specifically provided for, two R groups may be taken together to form a divalent group, such as one of the divalent groups further defined below. When such a divalent group is attached to the same ring atom, a spirocyclic ring structure will result.

When the point of attachment is depicted as "floating", for example, in the formula:

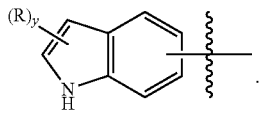

then the point of attachment may replace any replaceable hydrogen atom on any of the ring atoms of either of the fused rings unless specified otherwise.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH═CHF, —CH═CHCl and —CH═CHBr, are non-limiting examples of substituted alkenyl groups.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH═CH$_2$ (vinylphenyl), —C$_6$H$_4$CH═CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S, Non-limiting examples of substituted aryl groups include the groups: C$_6$H$_4$F, C$_6$H$_4$Cl, C$_6$H$_4$Br, C$_6$H$_4$I, —C$_6$H$_4$OH, —C$_6$H$_4$OCH$_3$, C$_6$H$_4$OCH$_2$CH$_3$, —C$_6$H$_4$OC(O)CH$_3$, C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, C$_6$H$_4$CONH$_2$, C$_6$H$_4$CONHCH$_3$, and —C$_6$H$_4$CON(CH$_3$)$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A compound having a formula that is represented with a dashed bond is intended to include the formulae optionally having zero, one or more double bonds. Thus, for example, the structure

includes the structures

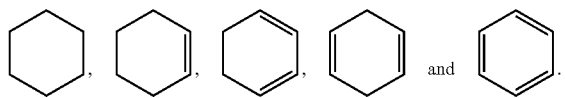

As will be understood by a person of skill in the art, no one such ring atom forms part of more than one double bond.

Any undefined valency on an atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

As used herein, the term "$IC_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: DMF, dimethylformamide; DMSO, dimethyl sulfoxide; MTT, 3-(4,5-Dimethylthiazol-2-yl)-2,5-diphenyltetrazolium bromide.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. β-LACTAM COMPOUNDS

In one aspect, the present disclosure provides compounds of the formula:

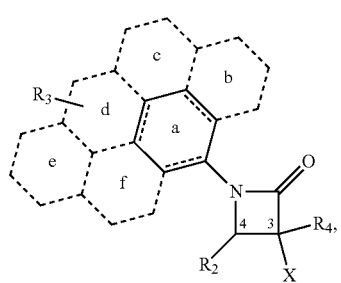

(I)

wherein:
X is —OS(O)$_2$R$_1$, —S(O)$_2$NH$_2$, —C(O)NH$_2$ or guanidinyl, wherein:
  R$_1$ is alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 8)}$, heteroaralkyl$_{(C\leq 8)}$, or a substituted version of any of these groups;
  R$_2$ is alkyl$_{(C\leq 12)}$, aralkyl$_{(C\leq 12)}$, heteroaryl$_{(C\leq 12)}$, heteroaralkyl$_{(C\leq 12)}$, or a substituted version of any of these groups;

R$_3$ and R$_4$ are each independently:
  amino, azido, cyano, halo, hydrogen, or hydroxy; or
  alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, acyloxy$_{(C\leq 12)}$, alkylamino$_{(C\leq 12)}$, dialkylamino$_{(C\leq 12)}$, amido$_{(C\leq 12)}$, or a substituted version of any of these groups; and
rings b, c, d, e and f, if present, are aromatic;
or a pharmaceutically acceptable salt or tautomer thereof.

In some embodiments, X is —OS(O)$_2$R$_1$. In some embodiments, R$_1$ is methyl. In some embodiments, R$_2$ is heteroaryl$_{(C\leq 12)}$. In some embodiments, R$_2$ is pyridyl. In some embodiments, R$_3$ is hydrogen. In some embodiments, R$_4$ is hydrogen. In some embodiments, the compounds of formula (I) are further defined by the formula:

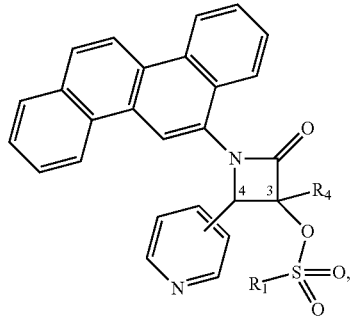

(II)

wherein:
R$_1$ is alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$ or heteroaralkyl$_{(C\leq 8)}$, or a substituted version of any of these groups; and
R$_4$ is:
  amino, azido, cyano, halo, hydrogen, or hydroxy; or
  alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, acyloxy$_{(C\leq 12)}$, alkylamino$_{(C\leq 12)}$, dialkylamino$_{(C\leq 12)}$, amido$_{(C\leq 12)}$, or a substituted version of any of these groups;
or a pharmaceutically acceptable salt or tautomer thereof.

In some embodiments, R$_1$ is alkyl$_{(C\leq 8)}$. In some embodiments, R$_1$ is methyl. In some embodiments, R$_4$ is hydrogen.

In some embodiments of formulas I or II, the carbon atom 3 is in the R conformation. In others it is in the S conformation. In some embodiments of formulas I or II, the carbon atom 4 is in the R conformation. In others it is in the S conformation.

In some embodiments, the compound is further defined as:

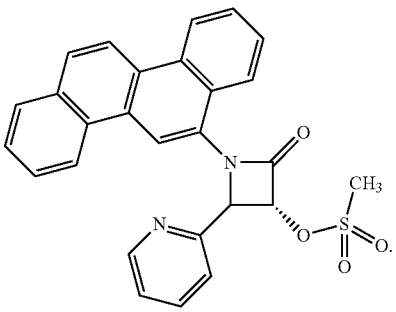 [SMILES: CS(=O)(=O)O[C@H]1C(=O)N(c2cc3c4ccccc4ccc3c3ccccc23)C1c1ccccn1]

In another aspect, the present invention provides methods for the preparation of one or more of the above compounds comprising:
(i) reacting a starting material of the formula:

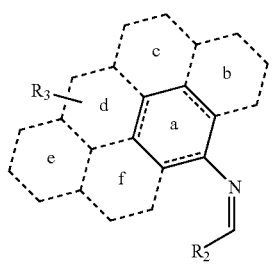

with acetoxyacetyl chloride and a first organic base to form a trans-lactam intermediate;
(ii) hydrolyzing the trans-lactam intermediate in aqueous base to form a hydroxy intermediate; and
(iii) reacting the hydroxy intermediate with a reagent selected from the group consisting of $R_1SO_2Cl$, $Cl-S(O)_2NH_2$, $Cl-C(O)NH_2$ and Cl-guanidinyl, and a second organic base to form a compound selected from those described above or discussed in the section entitled "Description of Illustrative Embodiments" below.

The Staudinger reaction has been used extensively for the synthesis of β-lactams (Scheme 1, for example, 6 and 7) (Georg and Ravikumar, 1992). This reaction typically requires an imine 5, a tertiary base (for example, triethylamine), and acid chloride 4 (or equivalent).

Scheme 1

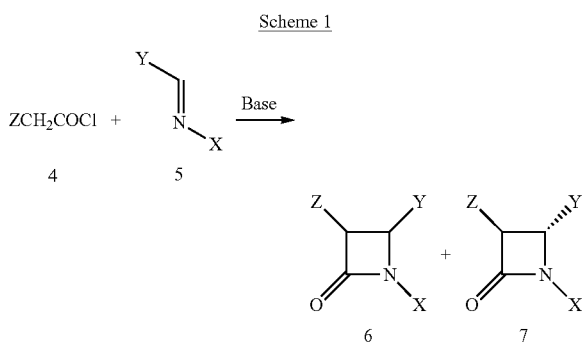

Figure 9:
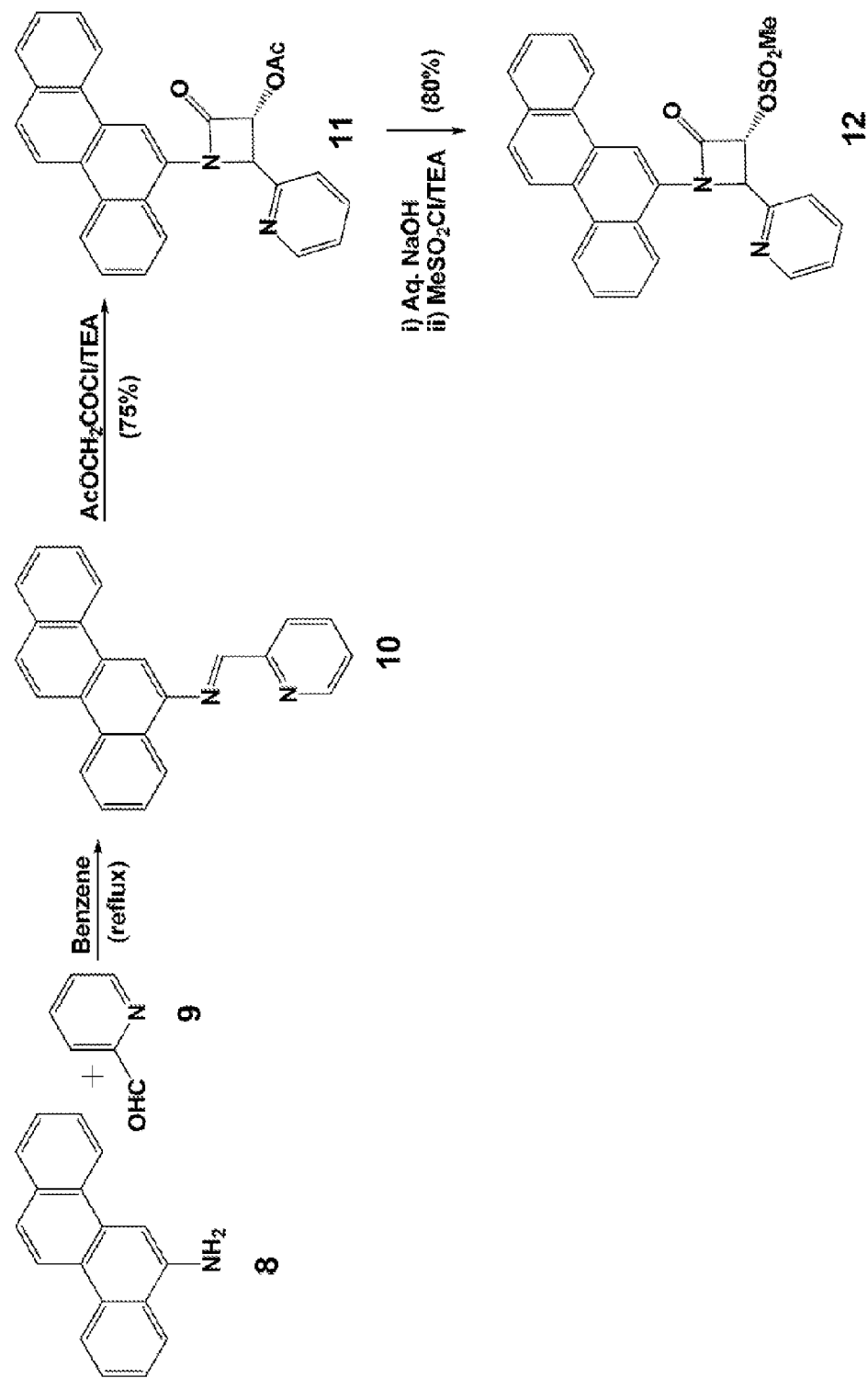
FIG. 9: This synthetic scheme shows the preparation of β-lactam 12 using a Staudinger reaction from 6-aminochrysene (8) and 2-pyridylaldehyde (9) as the starting compounds.

As outlined in FIG. 9 and discussed in Example 1 below, the preparation of β-lactam 12 (TX-262) was accomplished by following the Staudinger reaction using 6-aminochrysene (8) and 2-pyridylaldehyde (9) as the starting compounds. Refluxing of this amino compound 8 with the aldehyde 9 in toluene produced an imine. Cycloaddition was performed in the presence of acetoxyacetyl chloride and triethylamine. This reaction produced exclusively trans-β-lactam 11 in reasonably good yields. The acetoxy group in 11 was then hydrolyzed using dilute alkali and the resulting hydroxy compound was then converted to the mesyl derivative 12.

In some embodiments, the synthesis of trans-β-lactams disclosed herein may accomplished using microwave irradiation and changing the order in which the reagents were added. For example, microwave irradiation of a solution of imine 10 with acetoxyacetyl chloride in chlorobenzene afforded trans β-lactam 11 in comparable yield to the above method. (see Example 1 below). In short, a large Erlenmeyer flask may be taken as the reaction vessel in unmodified domestic microwave oven. In some embodiments, chlorobenzene or DMF may be used. The boiling points of either of these solvents is higher than the projected temperature of the reaction. The temperature of the reaction mixture may be kept below 110° C. by the adjustments of the on-off cycle and a "heat sink". Microwave energy is absorbed by all of the polar molecules effectively, therefore a stirrer is not needed nor is a reflux condenser required. These reactions were performed in unmodified domestic microwave ovens in a matter of minutes using very limited amounts of solvents.

Compounds of the present disclosure may be made using the methods described above and in Example 1 below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration, as defined by the IUPAC 1974 Recommendations.

Compounds of the present invention may also exist in prodrug form. Since prodrugs are known to enhance numerous desirable qualities of pharmaceuticals (e.g., bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in viva, to the parent compound.

Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

III. TREATMENT OF CANCER AND OTHER DISORDERS

In one aspect, compounds of the present disclosure may be used to induce apoptosis in tumor cells, to induce cell differentiation, to inhibit cancer cell proliferation, and/or to function in a chemopreventative capacity. For example, the β-lactam 12 (TX-262) was tested using human cancer cell lines. See Example 2 below and FIGS. 1-8. The β-lactams disclosed herein may also be used to reduce cancer cell proliferation and regresses tumor growth in vivo.

A. Pancreatic Cancer

In some embodiments, the therapeutic methods disclosed herein may be used to treat pancreatic cancer. Pancreatic cancer is a malignant neoplasm of the pancreas. It is estimated over 40,000 individuals in the United States will be diagnosed with this condition. Attention to human pancreatic tumors is especially warranted due to the almost invariably dismal outcome of currently available therapies. Save in the lesser instance of success when these tumors are diagnosed early and in highly localized presentation the vast majority of patients die in a relatively short time.

The compounds of the present invention may be used to treat pancreatic cancer. For example, the less than 1 μM $IC_{50}$ demonstrated by compound 12 against PANC1 is particularly striking PANC1 is referred to generically as the "gold standard of pancreatic cancers" representing as it does almost total resistance to GEM (gemcitabine), the first line treatment currently used in clinical situations. Compound 12 was also shown to be effective against all pancreatic tumor lines currently designated as GEM responsive. And its effectiveness against the GEM-resistant line Miapaca-2 was at approximately one-half the concentration required by GEM. See Example 2 below.

In vivo results further confirmed the anti-tumorigenic activity of TX-262. In a series of experiments detailed in Example 3, the compound was tested in athymic nude mice that had been injected with luciferase-labeled MPanc96 cells. This is known to be a highly aggressive line of human pancreatic cells. Results from these experiments are shown in FIGS. 1-8.

IV. PHARMACEUTICAL FORMULATIONS AND ROUTES OF ADMINISTRATION

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b)

the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

Other general aspects of the present disclosure contemplate a pharmaceutical composition comprising as an active ingredient a compound of the present disclosure and a pharmaceutically acceptable carrier. The composition may, for example, be adapted for administration by a route selected from the group consisting of orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or any combination thereof. In particular embodiments, the composition may be formulated for oral delivery. In particular embodiments, the composition is formulated as a hard or soft capsule, a tablet, a syrup, a suspension, a wafer, or an elixir. In certain embodiments, the soft capsule is a gelatin capsule. Certain compositions may comprise a protective coating, such as those compositions formulated for oral delivery. Certain compositions further comprise an agent that delays absorption, such as those compositions formulated for oral delivery. Certain compositions may further comprise an agent that enhances solubility or dispersibility, such as those compositions formulated for oral delivery. Certain compositions may comprise a compound of the present disclosure, wherein the compound is dispersed in a liposome, an oil and water emulsion or a water and oil emulsion.

Yet another general aspect of the present disclosure contemplates a therapeutic method comprising administering a pharmaceutically effective amount of a compound of the present disclosure to a subject. The subject may, for example, be a human. These or any other methods of the present disclosure may further comprise identifying a subject in need of treatment.

Another method of the present disclosure contemplates a method of treating cancer in a subject, comprising administering to the subject a pharmaceutically effective amount of a compound of the present disclosure. The cancer may be any type of cancer, such as a carcinoma, sarcoma, lymphoma, leukemia, melanoma, mesothelioma, multiple myeloma, or seminoma. Other types of cancers include cancer of the bladder, blood, bone, brain, breast, central nervous system, colon, endometrium, esophagus, genitourinary tract, head, larynx, liver, lung, neck, ovary, pancreas, prostate, spleen, small intestine, large intestine, stomach, or testicle. In these or any other methods, the subject may be a primate. This or any other method may further comprise identifying a subject in need of treatment. The subject may have a family or patient history of cancer. In certain embodiments, the subject has symptoms of cancer. The compounds of the invention may be administered via any method described herein, such as locally. In certain embodiments, the compound is administered by direct intratumoral injection or by injection into tumor vasculature. In certain embodiments, the compounds may be administered systemically. The compounds may be administered intravenously, intra-arterially, intramuscularly, intraperitoneally, subcutaneously or orally, in certain embodiments.

In certain embodiments regarding methods of treating cancer in a subject, comprising administering to the subject a pharmaceutically effective amount of a compound of the present disclosure, the pharmaceutically effective amount is 0.1-1000 mg/kg. In certain embodiments, the pharmaceutically effective amount is administered in a single dose per day. In certain embodiments, the pharmaceutically effective amount is administered in two or more doses per day. The compound may be administered by contacting a tumor cell during ex vivo purging, for example. The method of treatment may comprise any one or more of the following: a) inducing cytotoxicity in a tumor cell; b) killing a tumor cell; c) inducing apoptosis in a tumor cell; d) inducing differentiation in a tumor cell; or e) inhibiting growth in a tumor cell. The tumor cell may be any type of tumor cell, such as a leukemia cell. Other types of cells include, for example, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

V. COMBINATION THERAPY

In addition to being used as a monotherapy, the compounds of the present disclosure may also find use in combination therapies. Effective combination therapy may be achieved with a single composition or pharmacological formulation that includes both agents, or with two distinct compositions or formulations, for example, given at the same time. Alternatively, the second therapy may precede or follow treatment with the first agent by intervals ranging from minutes to months.

Regarding methods of treating cancer in a subject, comprising administering to the subject a pharmaceutically effective amount of a compound of the present disclosure, the method may further comprise a treatment selected from the group consisting of administering a pharmaceutically effective amount of a second drug, radiotherapy, gene therapy, and surgery. Such methods may further comprise (1) contacting a tumor cell with the compound prior to contacting the tumor cell with the second drug, (2) contacting a tumor cell with the second drug prior to contacting the tumor cell with the compound, or (3) contacting a tumor cell with the compound and the second drug at the same time. The second drug may, in certain embodiments, be an antibiotic, anti-inflammatory, anti-neoplastic, anti-proliferative, anti-viral, immunomodulatory, or immunosuppressive. The second drug may be an alkylating agent, androgen receptor modulator, cytoskeletal disruptor, estrogen receptor modulator, histone-deacetylase inhibitor, HMG-CoA reductase inhibitor, prenyl-protein transferase inhibitor, retinoid receptor modulator, topoisomerase inhibitor, or tyrosine kinase inhibitor. In certain embodiments, the second drug is 5-azacitidine, 5-fluorouracil, 9-cis-retinoic acid, actinomycin D, alitretinoin, all-trans-retinoic acid, annamycin, axitinib, belinostat, bevacizumab, bexarotene, bosutinib, busulfan, cap ecitabine, carboplatin, carmustine, CD437, cediranib, cetuximab, chlorambucil, cisplatin, cyclophosphamide, cytarabine, dacarbazine, dasatinib, daunorubicin, decitabine, docetaxel, dolastatin-10, doxifluridine, doxorubicin, doxorubicin, epirubicin, erlotinib, etoposide, etoposide, gefitinib, gemcitabine, gemtuzumab ozogamicin, hexamethylmelamine, idarubicin, ifosfamide, imatinib, irinotecan, isotretinoin, ixabepilone, lapatinib, LBH589, lomustine, mechlorethamine, melphalan, mercaptopurine, methotrexate, mitomycin, mitoxantrone, MS-275, neratinib, nilotinib, nitrosourea, oxaliplatin, paclitaxel, plicamycin, procarbazine, semaxanib, semustine, sodium butyrate, sodium phenylacetate, streptozotocin, suberoylanilide hydroxamic acid, sunitinib, tamoxifen, teniposide, thiopeta, tioguanine, topotecan, TRAIL, trastuzumab, tretinoin, trichostatin A, valproic acid, valrubicin, vandetanib, vinblastine, vincristine, vindesine, or vinorelbine.

In some embodiments for the treatment or prevention of cancer, compounds of the invention may be combined with one or more of the following: radiation, chemotherapy agents (e.g., cytotoxic agents such as anthracyclines, vincristine, vinblastin, microtubule-targeting agents such as paclitaxel and docetaxel, 5-FU and related agents, cisplatin and other platinum-containing compounds, irinotecan and topotecan, gemcitabine, temozolomide, etc.), targeted therapies (e.g., imatinib, bortezomib, bevacizumab, rituximab), or vaccine therapies designed to promote an enhanced immune response targeting cancer cells.

Various combinations may be employed, such as when a compound of the present disclosure is "A" and "B" represents a secondary agent, non-limiting examples of which are described below:

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the compounds of the present disclosure to a patient will follow general protocols for the administration of pharmaceuticals, taking into account the toxicity, if any, of the drug. It is expected that the treatment cycles would be repeated as necessary.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of (3R)-1-(chrysen-6-yl)-2-oxo-4-(pyridin-2-yl)azetidin-3-yl methanesulfonate (β-lactam 12; TX-262)

The preparation of β-lactam 12 was initiated using 6-aminochrysene (8) and 2-pyridylaldehyde (9) as the starting compounds. Refluxing of this amino compound 8 with the aldehyde 9 in toluene produced an imine. Cycloaddition was performed in the presence of acetoxyacetyl chloride and triethylamine. This reaction produced exclusively trans-β-lactam 11 in reasonably good yields. According to earlier results, cis-β-lactams were expected. The trans stereochemistry of the products has been verified from the NMR data.

The coupling constant of the C3 and C4 hydrogens in the cis-compounds is higher than that of in the trans-products. The acetoxy group in 11 was then hydrolyzed using dilute alkali and the resulting hydroxy compound was then converted to the mesyl derivative 12 (FIG. 9).

Preparation of β-Lactam 11

A solution consisting of acid chloride (1.5 mmol) in dichloromethane (8 mL) was added drop wise to a stirred solution containing imine 10 (1 mmol) and distilled triethylamine (3 mmol) in dry dichloromethane (10 mL) at −78° C. The reaction mixture was then stirred overnight at room temperature, washed with saturated sodium bicarbonate solution (10 mL), dilute hydrochloric acid (10%, 10 mL), brine (10 mL), dried with anhydrous sodium sulfate and evaporated to obtain the crude product. Proton NMR was performed to calculate the ratio of the isomeric β-lactams. The pure product 11 (75%) was then isolated via column chromatography over silica gel using ethyl acetate-hexanes (1:4) as the solvent.

Complete characterization data of the acetoxy beta-lactams: trans-N-(6-Chrysenyl)-3-acetoxy-4-(2′-pyridyl)-2-azetidine-2-one (11): mp 162-164° C.; IR cm$^{-1}$ (neat) 1760, 1600, 1510, 1485, 1450, 1390; $^1$H NMR (CDCl$_3$) δ (ppm) 2.29 (s, 3H), 5.30 (d, 1H, J=1.5 Hz), 5.58 (d, J=1.5 Hz, 1H), 7.16 (dd, J$_1$=5.1 Hz, J$_2$=6.9 Hz, 9H), 7.27 (d, 1H, J=9 Hz), 7.50-7.98 (m, 7H), 8.36-8.81 (m, 6H); Anal. Calcd for C$_{28}$H$_{20}$N$_2$O$_3$: C, 77.76; H, 4.66; N, 6.48. Found: C, 77.43; H, 4.35; N, 6.18.

Microwave-Assisted Preparation of the β-Lactam 11.

The same amount of imine 10, acid chloride, and triethylamine was placed in an Erlenmeyer flask (125 mL capacity) containing chlorobenzene (2 mL). The flask was then capped with a glass funnel and placed in a microwave oven (G. E. Model, 1450 W). A 500 mL beaker containing 200 mL of water was placed in the oven next to the reaction flask to serve as a "heat sink." The mixture was irradiated for 3 minutes at intervals of 1 minute each. After the usual work up as described above, the β-lactam was isolated (60% yield).

Preparation of the Mesyl β-Lactam 12

The acetoxy compound 11 (1 mmol) was hydrolyzed with cold dilute sodium hydroxide solution in water/THF (1:1, 10%) for 1 h. The product hydroxy compound was isolated after extraction with ethylacetate. The crude hydroxyl compound was converted to the mesyl compound 12 by treatment with methanesulfonyl chloride and triethylamine in 80% yield.

Example 2

In Vitro Anticancer Activity of (3R)-1-(chrysen-6-yl)-2-oxo-4-(pyridin-2-yl)azetidin-3-yl methanesulfonate (β-lactam 12; TX-262)

The β-lactam 12 was tested using human cancer cell lines with cisplatin and a linear diamide 1b as controls. Chemical name of compound 1b is given: 1-N-6′-Chrysenyl-4′-4-N-methylpiperazine-butane-1,4-dicarboxyamide. The results are depicted in Table 1.

TABLE 1

IC$_{50}$ µM of cisplatin, 1b and 12 in Cancer Cells Using the MTT Assay.

| Cell Line | A-549 | BRO | HT-29 | MDA-231 | PC-3 | PANC-1 |
|---|---|---|---|---|---|---|
| Cisplatin(3) | >100 | 5.7 | 17.0 | 10.1 | 2.1 | >100 |
| 1b(10) | >100 | 33.64 | 16.70 | 12.23 | 27.29 | >100 |
| 12(3) | 0.96 | 0.64 | 0.36 | 0.43 | 0.51 | 0.43 |

A549, Non-Small Cell Carcinoma of the Lung;
BRO, melanoma;
HT-29, colon carcinoma;
MDA-231, breast cancer;
PC-3, carcinoma of the prostate;
PANC-1, pancreatic cancer;
the number of runs is indicated ( ).

$8 \times 10^3$ cells/well were plated in a 97 well plate. Stock solutions of the agents were made in DMSO. Dilution of the compounds were in media with 10% FBS (fetal bovine serum). The cells were incubated in the drug for 72 hours and cell viability was determined by the MTT assay. IC$_{50}$ was then calculated.

Initially compound 12 was screened for its anti-tumor activities against a panel of human cancer lines in vitro and its activity compared to cisplatin and the linear diamide 1b. As is evident in Table 1, the activity of 12 against every tumor line far exceeded that of 1b and cisplatin as well. Of particular interest were its effects against A549 and PANC1, tumors which are generally resistant to the majority of known anti-tumor agents.

When tested against seven lines of human pancreatic cancer (Table 2), compound 12 demonstrated an IC$_{50}$ of less than 1.0 µM against 3/7; in the range of 1 µM-3.0 µM against 3/7 and 12.0 µM against one, Miapaca-2. However, this level of activity against this tumor was less than that seen with GEM which was 25.7.

A striking result included the consistent effectiveness of compound 12 against PANC1 the IC$_{50}$ of which averaged 0.75 µM when in comparison GEM was for all intents and purposes, inactive.

TABLE 2

IC$_{50}$ μM of 12 against Human Pancreatic Cancer Lines Using the MTT Assay.

| Cell Line | PANC-1 | ASCP-1 | BXPC-3 | Miapaca-2 | Pan02.03 | SW-1990 | CoLo35FG |
|---|---|---|---|---|---|---|---|
| 12 | (5) 0.75 | (3) 1.5 | (2) 0.43 | (4) 12.0 | (2) 0.39 | (2) 1.3 | (1) 2.7 |
| GEM | (3) >300 | (2) 0.1 | (2) 0.3 | (3) 25.7 | (2) 0.15 | (2) 0.4 | |

PANC-1*, ASCP-1, BXPC-3, Miapaca-2*, Pan02.03*; SW-1990, CoLo35FG are each cell lines derived from human pancreatic cancers.
Lines marked * are highly resistant to the three major classes of anti-tumor agents.

Example 3

In Vivo Anticancer Activity of TX-262

The anti-tumorigenic activity of TX-262 was assessed in 4 week old male athymic nude mice by using a luciferase gene, stably-expressing, highly aggressive line of human pancreatic cells, MPanc96. 2×10$^5$/50 ul luciferase-labeled MPanc96 cells were injected directly into the mouse pancreas. MPanc96 cells are among the most aggressive pancreatic tumor lines and have been demonstrated to be resistant to every major anti-tumor agent currently available. Bioluminescent imagining was utilized to estimate tumor volume and location and mice were then divided into two groups such that the mean tumor size was equal between the groups. For the next five weeks mice in the control group were treated with DMSO only; while Group II mice were treated Monday through Friday as follows: 100 mg/K bw i.p. at zero time [AM] and a booster dose of 25 mg/K bw i.p. 90 minutes later. Each week body weight and mortality were recorded and tumor growth was monitored by bioluminescence imaging. Results are shown in FIGS. 1-8.

Bioluminescence imaging utilized a cryogenically cooled image system coupled to a data acquisition computer running LivingImage Software [Xenogen Corp., Alameda Calif.]. Prior to imaging, the mice were anesthetized in an acrylic chamber using 1.5% isofluoroane/air mixture and injected i.p. with 40 mg/ml of luciferin potassium salt in PBS at a dose of 150 mg/K bw.

A digital grayscale animal image was acquired followed by acquisition and overlay of a pseudo color image representing the spacial distribution of detected photons emerging from active luciferase within the mouse. This measurement was converted into a measure of the mass of viable tumor cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

Banik et al., *J. Org. Chem.*, 58:307-309, 1993.
Banik et al., *J. Org. Chem.*, 59:4714-4716, 1994.
Banik, In: β-*Lactams: Synthesis, Stereochemistry, Synthons and Biological Evaluation*, Bentham Sci. Publ. Ltd., Vol. 11, 2004.
Bose et al., In: *The Amide Linkage: Selected Structural Aspects in Chemistry, Biochemistry, and Material Science*; Greenberg et al. (Eds.), Wiley-Interscience, NY, 7:157-214, 2000.
Bose et al., Tetrahedron, Symposium, 56:5603-5619, 2000 (In Print).
Burnett et al., *J. Med. Chem.*, 37:17334-1736, 1994.
Burnett, *Curr. Med. Chem.*, 11:1873-1887, 2004.
Buynak, *J. Curr. Med. Chem.*, 11:1951-1964, 2004.
Clader et al., *J. Med. Chem.*, 39:3684-3693, 1996
Clader, *J. Med. Chem.*, 47:1-9, 2004.
Finke et al., *J. Med. Chem.*, 38:2449-2462, 1995.
Georg and Ravikumar, In: *The Organic Chemistry of* β-*Lactams*, VCH publishers, NY, 1992.
Glazer et al., *Clin Cancer Res.*, 16(23):5712-5721, 2010.
*Handbook of Pharmaceutical Salts: Properties, and Use* (Stahl and Wermuth (Eds.), Verlag Helvetica Chimica Acta, 2002.
Jia et al., *Cancer Res.*, 70(3):1111-1119, 2010.
Kidwai et al., *Curr. Med. Chem.*, 6:195-215, 1999.
Kunnumakkara et al., *Cancer Res.*, 70(21):8695-8705, 2010.
Li and Abbruzzese, *Clinical Cancer Res.*, 16(17):4313-4318, 2010.
Manhas et al., *Tetrahedron, Symposium*, 56:5587-5601, 2000 (In Print).
*March's Advanced Organic Chemistry: Reactions, Mechanisms, and Structure*, 2007.
Ojima, *Acc. Chem. Res.*, 28:383-389, 1995.
Southgate et al., In: *Recent Progress in the Chemical Synthesis of Antibiotics and Related Microbial Products*, Lukacs (Ed.), Springer-Verlag, Berlin, 621(2), 1993.
Stadel et al., *Clin Cancer Res.*, 16(23):5734-5749, 2010.
Strejan et al., *Prog. Clin. Biol. Res.*, 146:429-434, 1984.
Suffness, In: *Taxol Science and Applications*, CRC Press, Boca Raton, Fla., 1995.
Tran et al., *Mol Cancer Ther.* 2010 July; 9(7):2068-2078, 2010.
Wan et al., *Cancer Res.*, 70(22):9371-9380, 2010.

The invention claimed is:
1. A compound of the formula:

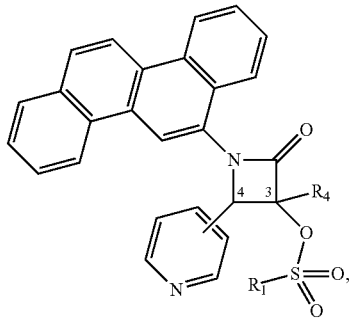

wherein:
R₁ is alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$ or heteroaralkyl$_{(C\leq 8)}$, or a substituted version of any of these groups; and
R₄ is:
hydrogen;
or a pharmaceutically acceptable salt or tautomer thereof.

2. The compound of claim 1, further defined as:

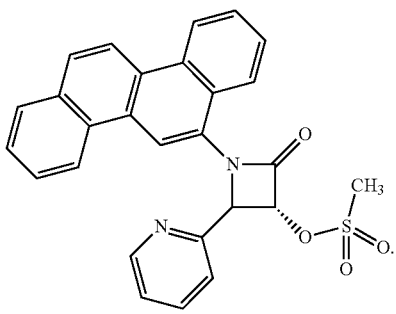 [SMILES: CS(=O)(=O)O[C@H]1C(=O)N(c2cc3c4ccccc4ccc3c3ccccc23)C1c1ccccn1]

3. A method for treating cancer, wherein the cancer is colorectal cancer, breast cancer, pancreatic cancer, lung cancer, skin cancer, or prostate cancer, in a patient in need thereof comprising administering to the patient an effective amount of a compound of the formula:

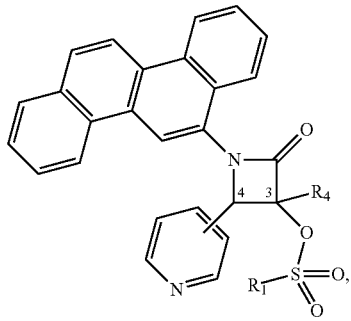

wherein:
R₁ is alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$ or heteroaralkyl$_{(C\leq 8)}$, or a substituted version of any of these groups; and
R₄ is hydrogen;
or a pharmaceutically acceptable salt thereof.

4. The method of claim 3, wherein the compound is further defined as:

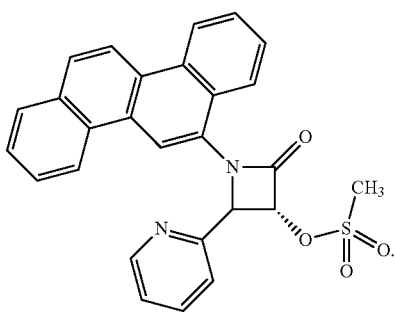 [SMILES: CS(=O)(=O)O[C@H]1C(=O)N(c2cc3c4ccccc4ccc3c3ccccc23)C1c1ccccn1]

5. The method of claim 3, wherein the cancer is pancreatic cancer.

6. The method of claim 5, wherein the pancreatic cancer is resistant to gemcitabine.

* * * * *

UNITED STATES PATENT AND TRADEMARK OFFICE
CERTIFICATE OF CORRECTION

PATENT NO.         : 8,946,409 B2
APPLICATION NO.    : 13/982101
DATED              : February 3, 2015
INVENTOR(S)        : Frederick F. Becker et al.

Page 1 of 1

It is certified that error appears in the above-identified patent and that said Letters Patent is hereby corrected as shown below:

In the Claims

In claim 1, column 27, line 25, delete "or tautomer".

Signed and Sealed this
Sixteenth Day of June, 2015

Michelle K. Lee
*Director of the United States Patent and Trademark Office*